United States Patent [19]

Al-Turaiki

[11] Patent Number: 4,865,611
[45] Date of Patent: Sep. 12, 1989

[54] LOCKABLE ROTATING ANKLE JOINT FOR MODULAR BELOW-KNEE PROSTHESIS

[76] Inventor: Mohammed H.S. Al-Turaiki, P.O. Box 65, Al-Zulfi, Saudi Arabia

[21] Appl. No.: 194,212

[22] Filed: May 16, 1988

[51] Int. Cl.⁴ ............................................. A61F 2/80
[52] U.S. Cl. ...................................... 623/38; 623/47; 248/418
[58] Field of Search ..................... 623/27–29, 623/38, 41, 43, 47, 49, 30, 40, 42, 50, 60, 62; 248/418; 294/19.1

[56] References Cited

U.S. PATENT DOCUMENTS

| 1,629,939 | 5/1927 | Turner | 248/418 X |
| 3,230,908 | 1/1966 | Grant | 248/418 X |
| 3,956,775 | 5/1976 | Moore | 623/27 X |

FOREIGN PATENT DOCUMENTS

| 1274616 | 9/1961 | France | 623/38 |
| 492069 | 4/1953 | Italy | 623/27 |
| 0721094 | 3/1980 | U.S.S.R. | 623/38 |
| 0155917 | 12/1920 | United Kingdom | 623/38 |
| 214096 | 4/1924 | United Kingdom | 623/38 |
| 2181060 | 4/1987 | United Kingdom | 623/27 |

Primary Examiner—Richard J. Apley
Assistant Examiner—David J. Bender
Attorney, Agent, or Firm—Walter C. Farley

[57] ABSTRACT

This patellar tendon bearing (PTB) prosthesis has a socket, a modular shank component, and a foot component which is attached rotatably to the shank component.

It allows a more comfortable sitting of the amputee fitted with such a prosthesis by allowing the foot component of the prosthesis to be safely and smoothly axially rotated inwardly or outwardly (±90°) with respect to the shank component of the prosthesis and to distribute uniformly the load, while sitting, on the whole lower limb, and to be latched in one of several positions.

1 Claim, 2 Drawing Sheets

LOCKABLE ROTATING ANKLE JOINT FOR MODULAR BELOW-KNEE PROSTHESIS

BACKGROUND OF THE INVENTION

This invention relates to a below knee prosthesis, in particular a patellar tendon bearing prosthesis comprising a socket, a modular shank component, and a foot component.

1. Field of the Invention

At present there are a variety of prostheses used for the below knee amputees. None of them, however, allows axial rotation of the foot relative to the shank piece. The absence of the latter facility necessarily limits the function of such a prosthesis if the amputee happens to be a praying muslim. Praying in the sitting position causes a major source of discomfort to the below-knee amputee wearing such a prosthesis according to the state of the art, e.g. with a standard PTB (patellar tendon bearing) prosthesis. Many of these amputees complain of painful knees and strains on hips and back when sitting during the performance of prayers.

SUMMARY OF THE INVENTION

The invention as claimed is intended to remedy these drawbacks. It solves the problem of how to design a reliable, simple foot rotator for a modular below knee prosthesis (endoskeletal system) which facilitates a more comfortable sitting by allowing the foot component of the prosthesis to safely and smoothly axially rotate internally or externally (±90°) with respect to the shank component of the prosthesis and to distribute uniformly the load, while sitting, on the whole lower limb.

The advantage offered by the invention is mainly to enable muslims all over the world with below knee amputations to carry out their religious duties with minimal inconvenience. It offers an immediate, safe and low cost solution to these existing problems.

A further advantage offered by the invention is the fact that no modification of the foot component of the prosthesis is necessary for incorporating the rotary mechanism into any type of conventional PTB prosthesis and the invention can easily be incorporated on any conventional shank prosthesis.

BRIEF DESCRIPTION OF THE DRAWINGS

The various features of novelty which characterize the invention are pointed out with particularity in the claims annexed to and forming part of this disclosure. For the better understanding of the invention, its operating advantages and specific objects attained by its use, reference should be had to the accompanying drawings and descriptive matter in which are illustrated and described preferred embodiments of the invention wherein

DESCRIPTION OF THE PREFERRED EMBODIMENTS

Figure 1:
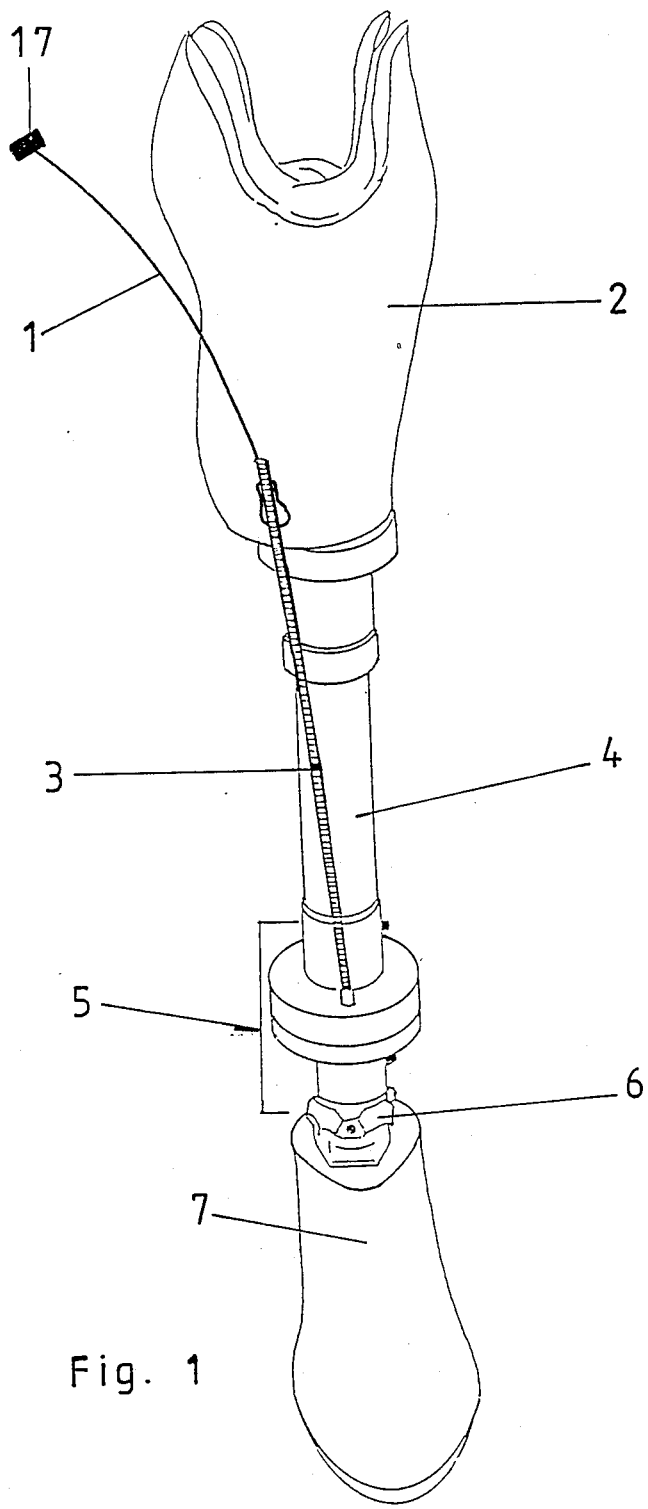
FIG. 1 is a schematic perspective diagram of the below knee prosthesis according to the invention.

FIG. 1 represents the below knee prosthesis according to the invention which consists basically of a modular patellar tendon bearing prosthesis comprising a socket 2 adaptable to the stump of the amputated leg, a modular shank piece 4 (e.g. of the modular below-knee prosthesis type) and a foot component 7 (e.g. of the modular prosthesis foot type).

The foot component 7 is attached rotatably to said shank piece 4 through incorporation of a foot rotator 5 and a foot connector 6, wherein rotation of the foot component 7 is controlled by a locking mechanism activated by handle 17 connected to cord 1 running through cord housing 3.

Figure 2:
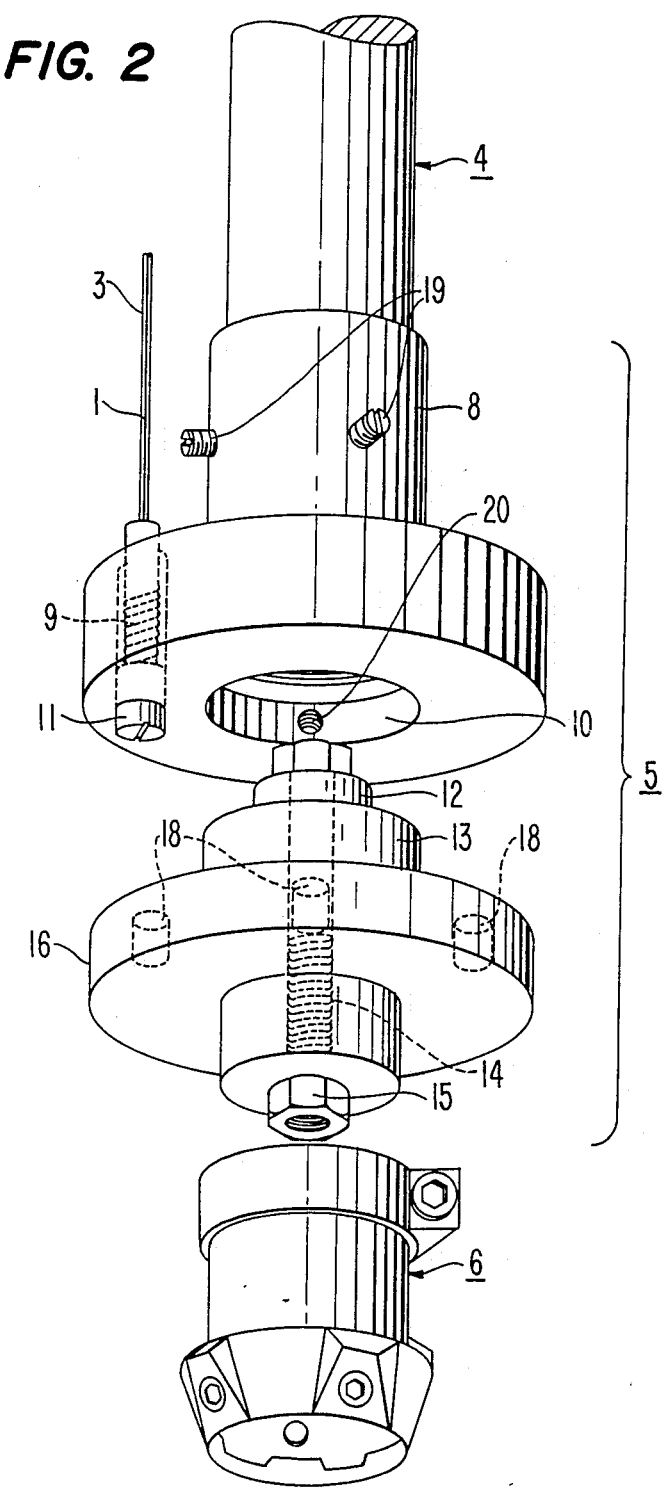
FIG. 2 is an exploded view of the below knee prosthesis according to the invention.

FIG. 2 shows in more detail that the foot rotator 5 is interposed in the foot-shank interface (4,6) and consists basically of low friction devices in the form of thrust bearing 13 fitting into bearing housing 10 and a locking mechanism consisting of locking pin 11 and annulus 16 with a number of holes 18 (preferably three) to prevent any rotation of the foot component 7 taking place during walking.

The annulus 16, representing the lower half of the foot rotator 5 is fastened to the foot component 7 by means of a foot connector 6. The three holes 18 in the annulus 16 are made for receiving the locking pin 11, which is loaded with a spring 9 and housed in the bearing housing 10. Pin 11 can be disengaged from hole 18 by pulling it out using the cable control handle 17 attached to the pulling cord 1. As shown in FIG. 1 pulling cord 1 is protected by cord housing 3 which can be safely fixed to the shank piece 4.

The prosthesis according to the invention allows the foot component 7 to be positioned pointing anteriorly, medially, or laterally as desired. This is achieved by simply pulling the control handle 17 up, pressing the foot component 7 against the ground and rotating the leg with shank piece component 4 with respect to the fixed foot component 7. Low friction motion is achieved through use of a thrust bearing 13 attached to the annulus 16 via a bolt 14, a nut 15 adn a washer 12.

The upper half of the foot rotator 5 is fastened to the modular shank piece 4 via a flange 8 with locking screws 19. This part also carries the bearing housing 10 and locking pin assembly 11,9.

The upper half of the foot rotator 5 is fastened to the lower half via a locking screw through the screw hole 20.

I claim:

1. A below-knee patellar tendon bearing prosthesis comprising
   a modular socket attachable to the stump of an amputated leg;
   a modular shank member attached to said modular socket;
   a modular foot component;
   pivot means for rotatably attaching said modular foot component to allow lateral rotation of said foot component relative to said shank piece and generally about the axis of said shank piece to about 90° either side of center, said pivot means including
      a first portion fixedly attached to said shank piece,
      a second portion fixedly attached to said foot component and
      bearing means for providing low-friction rotation between said first and second portions;
   a locking mechanism for selectively preventing said rotation during walking, said locking mechanism including
      an axially slidable pin carried by said first portion,
      means defining a plurality of holes in said second portion for receiving said pin in selected rotational positions of said second portion, spring means for urging said pin toward said holes,
a cable attached to said pin for manually moving said pin away from said holes against the force of said spring means, and
a cable sheath carried by a portion of said prosthesis above said pivot means for slidably receiving said cable.

* * * * *